United States Patent [19]

Steinman

[11] Patent Number: 5,797,889
[45] Date of Patent: Aug. 25, 1998

[54] MEDICAL DEVICE HAVING A CONNECTOR PORTION WITH AN IMPROVED SURFACE FINISH

[75] Inventor: Christopher P. Steinman, Sandy City, Utah

[73] Assignee: Becton Dickinson and Company, Franklin Lakes, N.J.

[21] Appl. No.: 667,523

[22] Filed: Jun. 19, 1996

[51] Int. Cl.⁶ ............................................. A61M 25/00
[52] U.S. Cl. ................................. 604/283; 604/280
[58] Field of Search ......................... 604/283, 411, 604/412–414, 905

[56] References Cited

U.S. PATENT DOCUMENTS

| 4,820,288 | 4/1989 | Isono | 604/280 |
| 5,520,641 | 5/1996 | Behnke et al. | 604/86 |
| 5,533,708 | 7/1996 | Atkinson et al. | 604/256 |

*Primary Examiner*—Manuel Mendez
*Attorney, Agent, or Firm*—Eric M. Lee

[57] ABSTRACT

This invention relates to the surface finish on a portion of a medical device that connects to another medical device. By controlling the average surface roughness on the mating surface of the connector portion of the medical device leakage at the connection can be eliminated and the connection can be readily disengaged by hand.

10 Claims, 5 Drawing Sheets

5,797,889

MEDICAL DEVICE HAVING A CONNECTOR PORTION WITH AN IMPROVED SURFACE FINISH

BACKGROUND OF THE INVENTION

The subject invention relates in general to the surface finish of the connector portion of a medical device. This invention has particular applicability to the surface roughness of a portion of the adapter of an IV catheter and the surface roughness of a portion of the adapter of a removable injection site. Elimination of leakage and maintenance of acceptable removal axial force or torque values at the connection between the two medical devices results by ensuring that the portion of the adapters of the IV catheter and removable injection site that mate have a particular surface roughness. Although this invention has particular applicability to the luer adapter of an IV catheter and a removable injection site, it is to be understood that this invention is applicable to other medical device connector configurations on IV catheters, IV administration sets, removable access valves, injection sites and other medical devices.

In the medical treatment of patients it is common for catheters to be inserted into the patient to allow medical personnel to have access to the patient's vasculature. This may be necessary so fluids or medicaments can be administered to the patient through the catheter or so that blood may be withdrawn from the patient through the catheter for analysis. Depending upon the type of fluid treatment needed for the patient, various other medical devices can be connected to the catheter. For example, an IV administration set can be connected to the catheter to provide a continuous source of fluid to the patient. Alternatively, a PRN type valve can be connected to the catheter to allow intermittent administration of medicaments to the patient. If blood is to be withdrawn from the patient, a syringe can be connected to the catheter to facilitate the removal of small amounts of blood.

The connection between the two medical devices, such as between an IV catheter and a removable injection site, should be fluid tight so that fluid will not leak from the system at the connection. Leakage is a problem for at least two reasons. First, with the increasing cost of medical care, wasting medical fluids, such as saline solution or expensive medicine, through spillage is not acceptable. Second, with the advent of AIDS and other blood borne diseases, spillage of body fluids may become a source for the spread of such diseases to other patients and medical personnel. In prior attempts to avoid leakage at the connection where luer slips are used, tape is wrapped around the connection. However, this is insufficient to prevent leakage because of the difficulty in ensuring a good seal.

The connection should also not allow air to enter the system. Avoiding air infiltration at the connection can be critical because in certain patient populations, such as those in neonatal intensive care units, air embolism can be fatal in some cases.

Even though the connection between the two medical devices should be fluid and air tight, the connection should be readily disengaged by hand so the two medical devices can be separated by medical personnel with little difficulty. The need to disconnect a medical device from a catheter may arise if, for example, a PRN type valve must be removed from the catheter because the valve has been damaged through repeated use or the treatment protocol has changed requiring a different set up, such as the use of a continuous fluid flow from an IV administration set instead of intermittent administration of fluid through a valve. If medical personnel are unable to separate the two medical devices without the use of other implements, such as a hemostat, either or both of the medical devices could be damaged. This may require that a new catheter be inserted into the patient. Having to replace one catheter that is already inserted into the patient with a new catheter is undesirable because it adds to patient discomfort and is wasteful.

Heretofore, the connector portions of medical devices have allowed other devices to be connected thereto. Unfortunately, these connections have had varying amounts of leakage and unacceptably high axial force or removal torque values. Prior attempts to prevent leakage at the connection required the surface of the connector portions to be highly polished. This resulted in some connections that are fluid and air tight but that are difficult to disengage. Other connections are easy to disengage but are prone to leakage.

SUMMARY OF THE INVENTION

It is therefore an object of this invention to provide a connector for a medical device that can be connected to another medical device without fluid leakage or air infiltration at the connection.

It is another object of this invention to provide a connector for a medical device that can be disconnected from another medical device with a predictably low axial separation force or removal torque value.

The above and other objects are achieved by this invention wherein the surface of the connector portion of a medical device that mates with the surface of a complementary connector portion of another medical device has an average surface roughness of at least about 10 micro-inches.

BRIEF DESCRIPTION OF THE DRAWINGS

The preferred embodiments are illustrated in the drawings in which like reference numerals refer to like elements and in which.

DETAILED DESCRIPTION OF THE INVENTION

This invention is described hereinafter as applied to the female and male luer portions of an IV catheter and a removable injection site respectively. However, it is to be understood that this invention is applicable to other connector configurations used on other medical devices.

Figure 1:
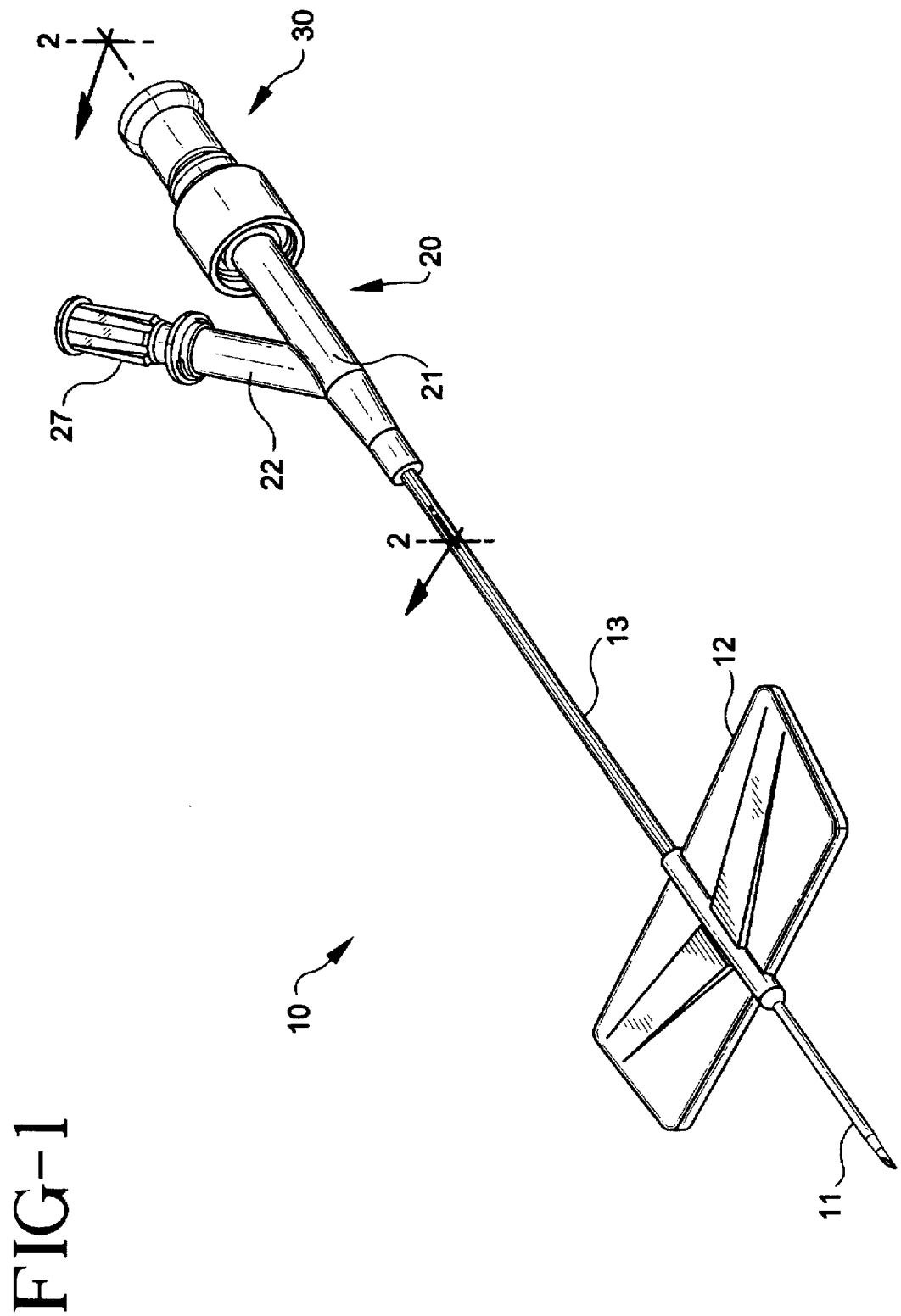
FIG. 1 is a perspective view of an IV catheter and removable injection site connected thereto incorporating the subject invention along the mating surfaces between the two devices.
Figure 2:
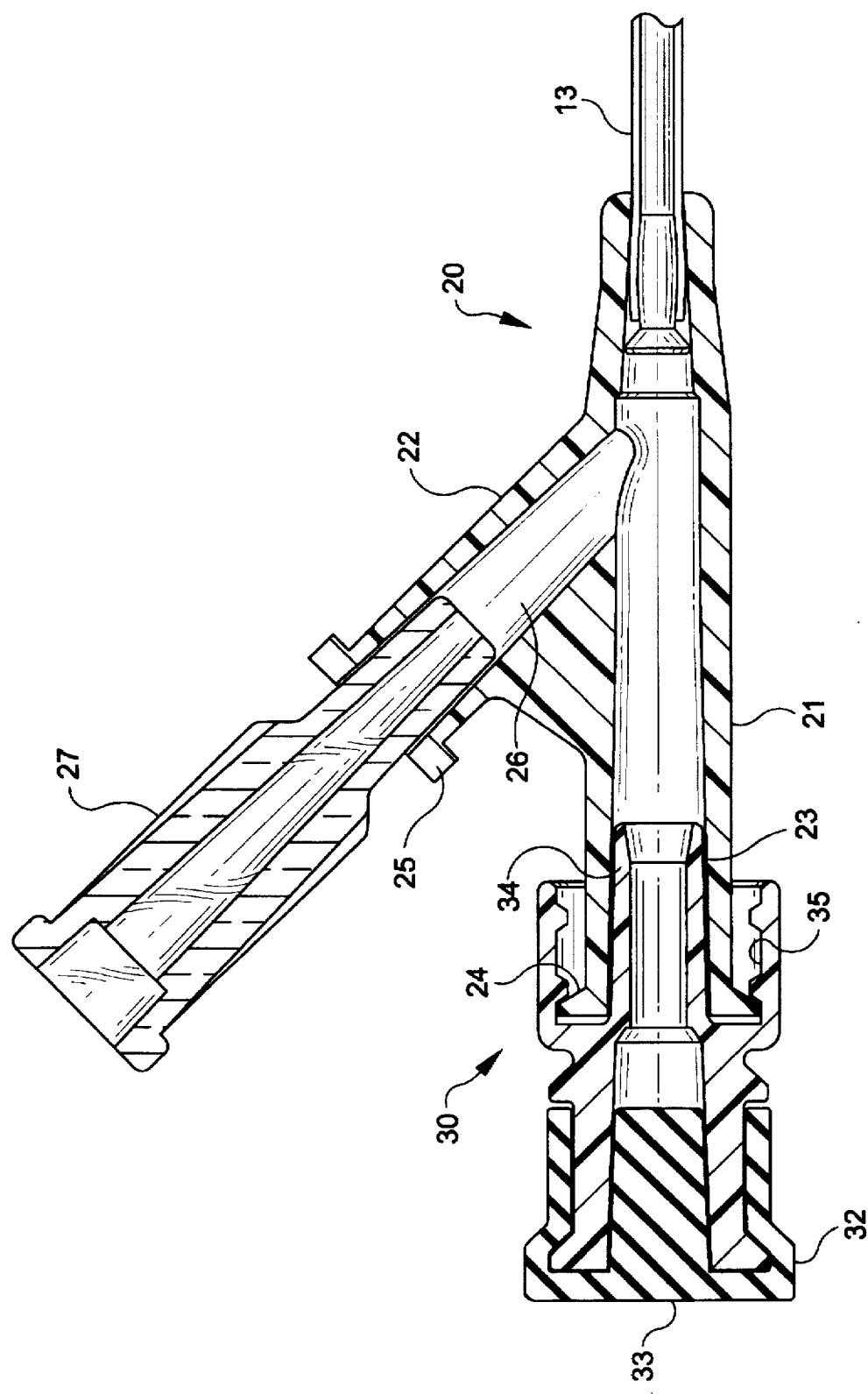
FIG. 2 is a cross-sectional view taken along line 2—2 of the portion of the IV catheter connected to the removable injection site shown in FIG. 1.
Figure 3:
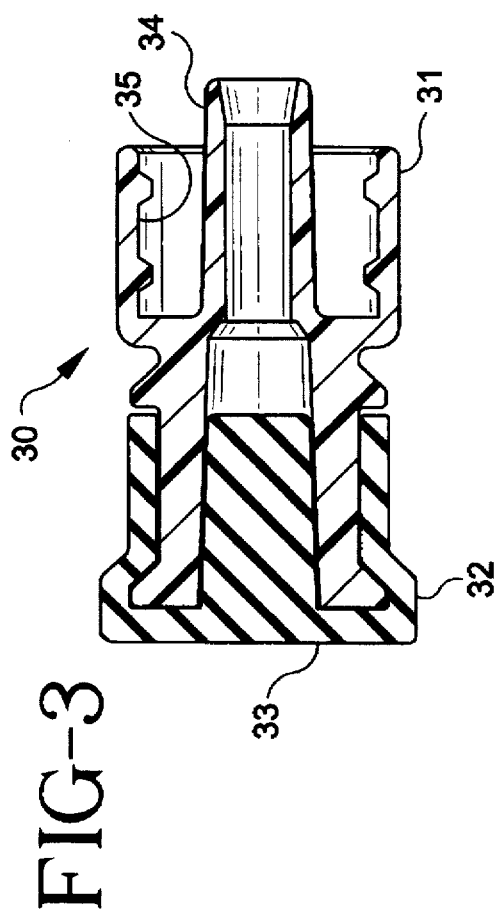
FIG. 3 is a cross-sectional view of a removable injection site incorporating the subject invention along the external surface of the male luer portion.
Figure 4:
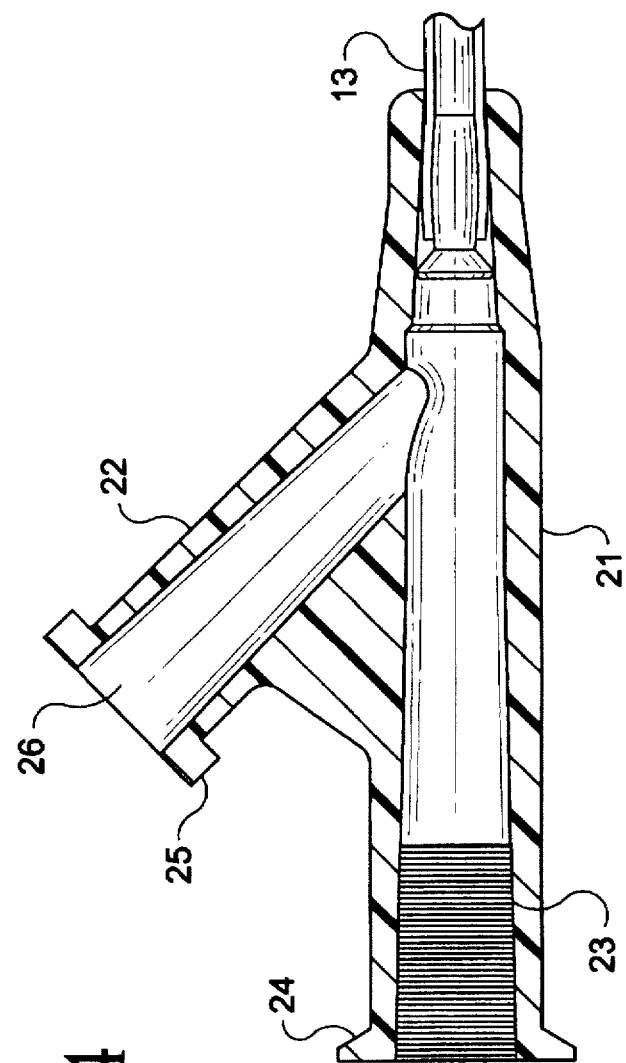
FIG. 4 is a cross-sectional view of an IV catheter adapter incorporating the subject invention along the internal surface of the female luer portion which is exaggerated for illustrative purposes.

The IV catheter 10 shown in FIG. 1 includes a cannula 11, a pair of wings 12, an extension tube 13 and an adapter 20. As shown in FIGS. 1, 2 and 4, adapter 20 is a Y-adapter having a main portion 21 and a side arm 22. Main portion 21 has a standard female luer portion 23 with external threads 24 thereabout. Side arm 22 also defines external threads 25 and female luer portion 26. A vent plug 27 is shown connected to side arm 22 in FIGS. 1 and 2.

The removable injection site 30 has a connector portion 31 and an access portion 32. Access portion 32 houses the valve mechanism 33. For illustrative purposes only, valve mechanism 33 has a pierceable septum configuration. However, other configurations, such as a slit septum or a piston type configuration, could be used for valve mechanism 33. Connector portion 31 has a standard male luer portion 34 with internal threads 35.

As shown in FIGS. 1 and 2, connector portion 31 is connected to main portion 21 of adapter 20. However, it is to be understood that connector portion 31 could be connected to side arm 22. FIG. 2 also shows that connector portion 31 contacts side arm 22 along two locations. One location is along threads 24 and 35. The other location is at the interface between female luer portion 23 and male luer portion 34. It has been found that by controlling the surface roughness of the internal surface of female luer portion 23 and the external surface of male luer portion 34, leakage between adapter 20 and removable injection site 30 can be eliminated. In addition, the removal torque necessary to disengage adapter 20 from removable injection site 30 can be kept to an acceptably low level that allows hand removal of removable injection site 30 from adapter 20. Such a torque level is below about 20 inch ounces. When the removal torque exceeds this value, it is extremely difficult for medical personnel to disengage removable injection site 30 from adapter 20 without the use of other implements, such as a hemostat, to grasp and rotate removable injection site 30 with respect to adapter 20. Although removal torque is discussed in connection with this embodiment, it is to be understood that the axial removal force values remain at an acceptably low level when the average surface roughness of the mating surfaces of luer slip connectors are controlled as discussed below.

Specifically, the average surface roughness along the internal surface of female luer portion 23 should be at least about 10 micro-inches and preferably between about 10 micro-inches and about 50 micro-inches. In addition, the average surface roughness along the external surface of male luer portion 34 should be between about 10 micro-inches and about 50 micro-inches. This translates into an average surface roughness of between about 4 and about 6 on the Society of Plastics Industry and Society of Plastics Engineers Mold Finish Comparison Kit or between about 12 and about 24 on the Charmilles Scale. This average surface roughness preferably extends along the length of male luer portion 34 and along the length of female luer portion 23 that mate. In order to determine the average surface roughness, a plurality of surface roughness measurements should be made along different portions of the surface being measured. For example, where the surface being measured is a female or male luer, 18 such measurements parallel to the longitudinal axis of the device should be taken over the mating surface at 20 degree intervals. Of course, the more measurements taken, the more accurate the resulting average surface roughness measurement will be.

The following examples illustrate the benefits of the particular average surface roughness characteristics of this invention.

EXAMPLE 1

50 catheter adapters were prepared by molding the adapters using a core pin that was polished along the surface that was used to form the female luer so it would have an average surface roughness of about 9 micro-inches. 50 removable injection sites were prepared by molding the injection sites using cavity steel that was polished along the surface that was used to form the male luer portion so it would have an average surface roughness of about 5 micro-inches or less. When the male luer was connected to the female luer for each of these samples, the mean removal torque was about 39 inch ounces with a standard deviation of about 5.4 inch ounces. This value is too high to permit the removable injection site to be removed from the catheter adapter by hand.

EXAMPLE 2

100 catheter adapters were prepared by molding the adapters using a core pin that was ground along the portion of the surface that was used to form the female luer so it would have a plurality of micro-grooves on that surface and provide an average surface roughness of between about 28 and about 41 micro-inches. 100 removable injection sites were prepared by molding the injection sites using cavity steel that was sandblasted along the portion that was used to form the male luer so it would have a dimpled surface with an average surface roughness of between about 22 and about 40 micro-inches. When the male luer was connected to the female luer for each of these samples, the mean removal torque was below about 13 inch ounces. This value allows the removable injection site to be easily removed from the catheter adapter by hand. In addition, none of the samples leaked.

EXAMPLE 3

1280 catheter adapters were prepared by molding the adapters using a core pin that was ground along the portion that was used to form the female luer so it would have a plurality of micro-grooves thereon. The mean average surface roughness for these samples was about 20 micro-inches but ranged from as high as about 46 micro-inches to as low as about 8 micro-inches. 1280 removable injection sites were prepared by molding the injection sites using a cavity steel that was sandblasted along the portion that was used to form the male luer portion so it would have a dimpled surface. The mean average surface roughness for these samples was about 17 micro-inches but ranged from as high as about 45 micro-inches to as low as about 8 micro-inches. When the male luer was connected to the female luer for each of these samples, the mean removal torque was below about 12 inch ounces. This value allows the removable injection site to be easily removed from the catheter adapter by hand. In addition, none of the samples leaked.

Figure 5:
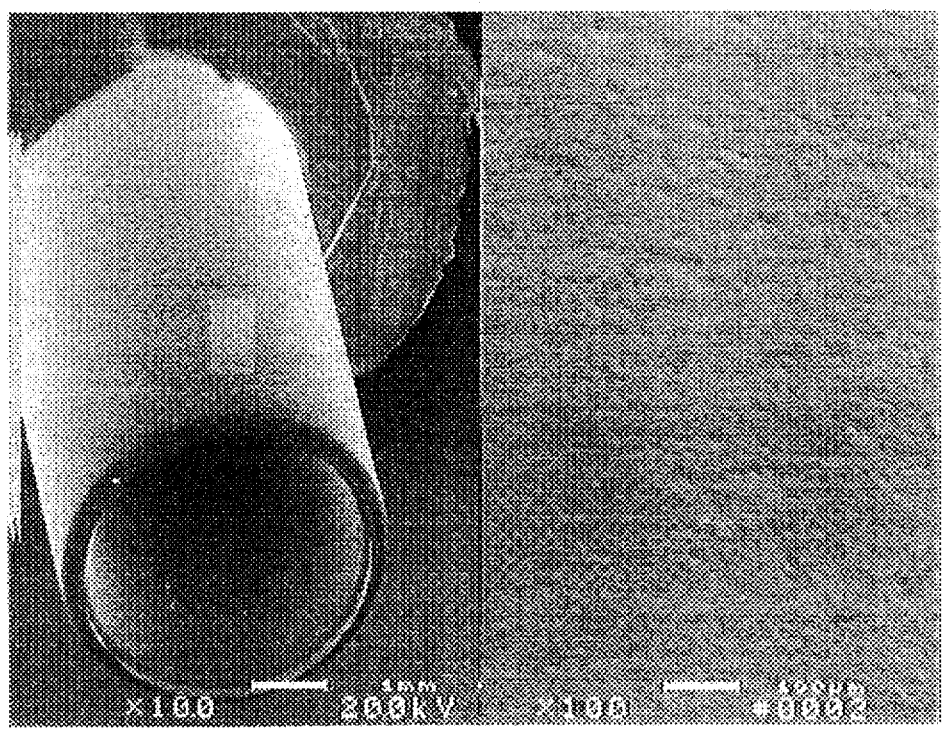
FIG. 5 is a photomicrograph of a portion of the external surface of a male luer that has been formed by using a cavity steel that has been sandblasted to provide a dimpled surface with the right side of the photomicrograph magnified 100 times and the left side of the photomicrograph magnified 10 times.
Figure 6:
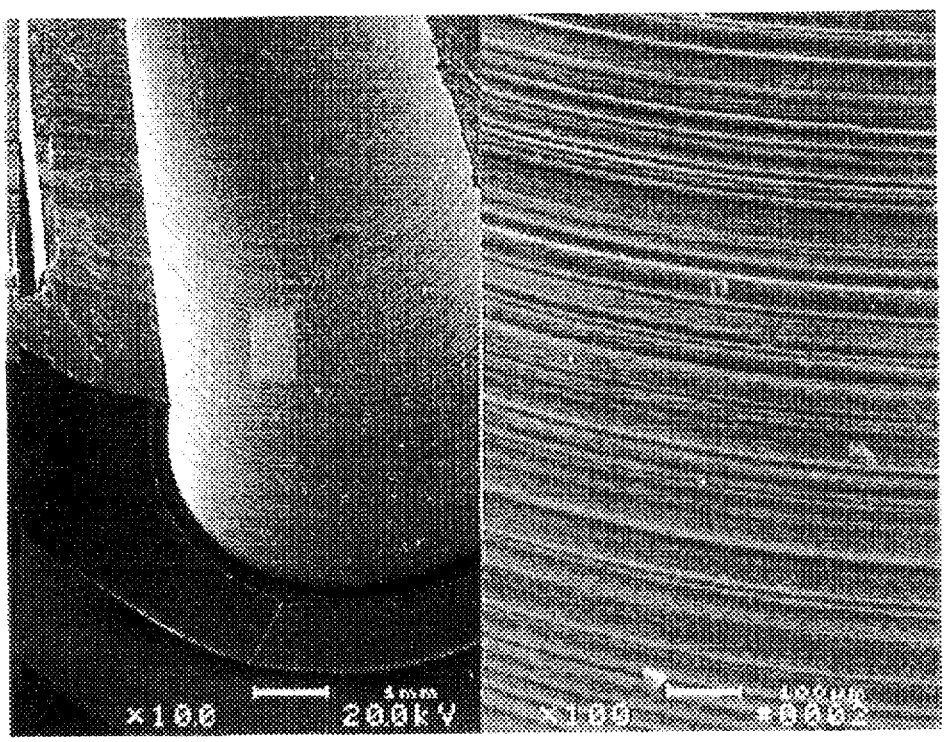
FIG. 6 is a photomicrograph of a portion of the internal surface of a female luer that has been formed by using a core pin that has been ground to provide a surface with a plurality of micro-grooves thereon with the right side of the photomicrograph magnified 100 times and the left side of the photomicrograph magnified 10 times.

The contour of the surface of female luer portion 23 and male luer portion 34 at a microscopic level can take any form as long as the average surface roughness is at least about 10 micro-inches and preferably is in the range of between about 10 micro-inches and about 50 micro-inches. For example, the surface could have a dimpled or pitted contour. See FIG. 5. This contour can be achieved by sandblasting the surface of the cavity steel that is used to mold the part. Alternatively, the surface could be formed with a plurality of radial micro-grooves therein. See FIG. 6. This contour can be achieved by grinding the surface of the core pin that is used to form the part. The lead angle of these micro-grooves can be perpendicular to the longitudinal axis or at an angle thereto. However, it has been determined that for best results, female luer portion 23 should be formed with micro-grooves on the surface while male luer portion 34 should be formed with a dimpled or pitted surface. It has also been determined that, if for some reason either only female luer portion 23 or only male luer portion 34 is formed with the requisite average surface roughness, that surface should be formed with micro-grooves. Better results, in terms of leakage control and removal axial force or torque values, can be achieved in this manner.

The desired average surface roughness of female luer portion 23 and male luer portion 24 can be achieved by various methods. For example, where adapter 20 and removable injection site 30 are formed from either polypropylene or polycarbonate by an injection molding process, the surface of the core pin or cavity that is used in that process is treated in the places that will form the female or male luer portion of the device to have a particular average surface roughness.

In order to form the cavity that forms the male luer with the desired average surface roughness, the surface of the cavity is preferably sand blasted or EDM finished. When sand blasting is the mechanism chosen to treat the cavity that makes the male luer, the following parameters have been successfully employed. 50 micron aluminum oxide beads are ejected from a nozzle at a pressure of 60 psig. The nozzle is between ¼ inch and ⅛ inch from the surface of the cavity and is at an angle of about 15 degrees to the cavity surface. Where the core pin that forms the female luer is ground, a #9A801-K4-VFM grinding wheel from Cincinnati Milacron on a Myford OD Grinder is used. No subsequent polishing is performed to the cavity or core pin to obtain the specified surface roughness.

Thus, it is seen that a medical device is provided having a connector portion with a particular average surface roughness along a portion thereof that can be connected to another medical device having a particular average surface roughness along a portion thereof to form a connection that does not leak and that can be easily disengaged by hand.

I claim:

1. A medical device, comprising:
    an adapter portion for connection to another medical device wherein the adapter portion has a female luer with an internal surface that mates with a male luer portion of another medical device and wherein the internal surface of the female luer has an average surface roughness of at least about 10 micro-inches.

2. The medical device of claim 1 wherein the internal surface of the female luer of the adapter portion has a plurality of micro-grooves formed therein.

3. The medical device of claim 2 wherein the average surface roughness is between about 10 micro-inches and about 50 micro-inches.

4. The medical device of claim 1 wherein the internal surface of the female luer of the adapter portion is dimpled.

5. The medical device of claim 4 wherein the average surface roughness is between about 10 micro-inches and about 50 micro-inches.

6. A medical device, comprising:
    an adapter portion for connection to another medical device wherein the adapter portion has a male luer with an external surface that mates with a female luer portion of another medical device and wherein the external surface of the male luer has an average surface roughness of at least about 10 micro-inches.

7. The medical device of claim 6 wherein the external surface of the medical device has a plurality of micro-grooves formed therein.

8. The medical device of claim 7 wherein the average surface roughness is between about 10 micro-inches and about 50 micro-inches.

9. The medical device of claim 6 wherein the external surface of the medical device is dimpled.

10. The medical device of claim 9 wherein the average surface roughness is between about 10 micro-inches and about 50 micro-inches.

* * * * *